United States Patent
Schiemann et al.

(10) Patent No.: US 7,968,551 B2
(45) Date of Patent: Jun. 28, 2011

(54) CHROMENONEINDOLES

(75) Inventors: Kai Schiemann, Seeheim-Jugenheim (DE); Henning Böttcher, Darmstadt (DE); Timo Heinrich, Gross-Umstadt (DE); Günter Hölzemann, Seeheim-Jugenheim (DE); Christoph Van Amsterdam, Darmstadt (DE); Gerd Bartoszyk, Weiterstadt (DE); Joachim Leibrock, Pfungstadt (DE); Christoph Seyfried, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 886 days.

(21) Appl. No.: 10/551,997

(22) PCT Filed: Mar. 8, 2004

(86) PCT No.: PCT/EP2004/002351
§ 371 (c)(1),
(2), (4) Date: Oct. 4, 2005

(87) PCT Pub. No.: WO2004/087692
PCT Pub. Date: Oct. 14, 2004

(65) Prior Publication Data
US 2006/0258680 A1 Nov. 16, 2006

(30) Foreign Application Priority Data
Apr. 4, 2003 (DE) .................. 103 15 285

(51) Int. Cl.
*A61K 31/497* (2006.01)
*C07D 403/00* (2006.01)

(52) U.S. Cl. .................. 514/254.09; 544/373

(58) Field of Classification Search .......... None
See application file for complete search history.

(56) References Cited

U.S. PATENT DOCUMENTS
5,532,241 A 7/1996 Bottcher et al.
6,251,908 B1 6/2001 Bottcher et al.

FOREIGN PATENT DOCUMENTS
DE 19730989 1/1999
EP 0648767 4/1995

OTHER PUBLICATIONS

West, Anthony R., "Solid State Chemistry and its Applications", Wiley, new York, 1988, pp. 358 & 365.*
Gaster, L.M. et. al., Ann. Reports Med. Chem., 1998, vol. 33, pp. 21-30.*
Ann M. Mortimer, Expert Opinion on Investigational Drugs, 2004, vol. 13, No. 4, pp. 315-329.*
Newman et. al.; Drug Discovery Today, 2003, 8(19) p. 898.*
Chawla et. al.; Current Research & Information on Pharmaceutical Science, 2004, 5(1), p. 9.*
Vippagunta et. al. Advanced Drug Delivery Reviews 48 (2001) 3-26.*
Dorwald F. A. Side Reactions in Organic Synthesis, 2005, Wiley: VCH, Weinheim p. IX of Preface.*
Borisy, et. al., Proceedings of the National Acadamy of Sciences of the United States of America, 100(13) 7977-7982.*
Wolff et. al., "Burger's Medicinal Chemistry and Drug Discovery," 5th Ed. Part 1, pp. 975-977 (1995).*
Banker, et. al., Modern Pharmaceuticals, (1996) p. 596.*
http://www.umm.edu/patiented/articles/what_causes_eating_disorders_000049_3.htm, last accessed Feb. 16, 2010.*
http://www.wrongdiagnosis.com/s/sexual_dysfunction/causes.htm, last accessed Feb. 16, 2010.*
http://en.wikipedia.org/wiki/Brain_trauma, last accessed on Jun. 10, 2010.*
http://en.wikipedia.org/wiki/Learning_disorders, last accessed on Jun. 10, 2010.*
http://en.wikipedia.org/wiki/memory_disorder, last accessed on Jun. 10, 2010.*
http://en.wikipedia.org/wiki/eating_disorder, last accessed on Jun. 10, 2010.*
http://en.wikipedia.org/wiki/sexual_dysfunction, last accessed on Jun. 10, 2010.*
http://en.wikipedia.org/wiki/sleeping_disorder, last accessed on Jun. 10, 2010.*
http://en.wikipedia.org/wiki/spinal_cord_trauma, last accessed on Jun. 10, 2010.*
Borisy, et. al., Proceedings of the National Academy of Sciences of the United States of America, (2003), 100(13) 7977-7982.*
Francois Giuliano et al., "The Pharmacological Treatment of Premature Ejaculation"; Journal Compilation, 2008; vol. 102, pp. 668-675.
Andrew W. Goddard et al., "Serotoninergic Mechanisms in the Treatment of Obsessive-Compulsive Disorder"; Drug Discovery Today, Apr. 2008, vol. 13, pp. 325-332.
Lucianne Groenink et al., "The Corticosterone-enhancing Effects of the $5\text{-HT}_{1A}$ receptor antagonist . . . ", European Journal of Pharmacology, vol. 272, 1995, pp. 177-183.
Timo Heinrich et al., "Dual $5\text{-HT}_{1A}$ agonists and 5-HT Re-uptake Inhibitors by Combination of . . . ", Bioorganic & Medicinal Chemistry, vol. 12, 2004, pp. 4843-4852.
$5\text{-HT}_{1A}$ Autoreceptors and the Mode of Action of Selective Serotonin Reuptake Inhibitors (SSRI), Behavioural Brain Research, vol. 73, 1996, pp. 281-283.

(Continued)

*Primary Examiner* — James O Wilson
*Assistant Examiner* — Jeffrey H Murray
(74) *Attorney, Agent, or Firm* — Millen, White, Zelano & Branigan, P.C.

(57) ABSTRACT

Chromenoneindole derivatives of the formula (I), in which $R^1$, $R^2$, $R^3$, R, A and B are as defined in Claim 1, and pharmaceutically usable prodrugs, derivatives, solvates, stereoisomers and salts thereof, exhibit particular actions on the central nervous system, in particular 5-HT reuptake-inhibiting and $5\text{-HT}_x$-agonistic and/or -antagonistic actions. They are distinguished by particularly high bioavailability and particularly high inhibition of 5-HT reuptake.

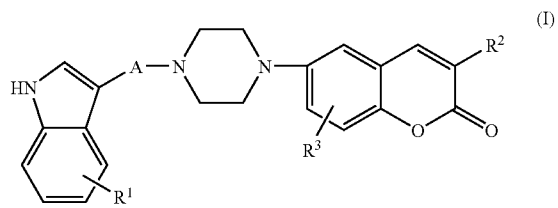

15 Claims, 3 Drawing Sheets

OTHER PUBLICATIONS

Sean L. Kitson, "5-Hydroxytryptamine (5-HT) Receptor Ligands", Current Pharmaceutical Design, vol. 13, 2007, pp. 2621-2637.

Helmi L. Lutsep, "Repinotan, a 5-HT1A Agonist, in the Treatment of Acute Ischemic Stroke", Current Drug Targets—CNS & Neurological Disorders, 2005, vol. 4, pp. 119-120.

Lisa Matzen et al., "5-HT Reuptake Inhibitors With 5-HT Antagonistic Activity . . . ", Journal of Medicinal Chemistry, 2000, vol. 43 (6), pp. 1149-1157.

Gerd D. Bartoszyk et al., "EMD 281014, a New Selective Serotonin 5-$HT_{2A}$ Receptor Antagonist", European Journal of Pharmacology, vol. 473, 2003, pp. 229-230.

Regis Bordet et al., "Effect of Pindolol on Onset of Action of Paroxetine . . . ", Am J Psychiatry, 1998; vol. 155, pp. 1346-1351.

Alan D. Brown et al., "Designing Drugs for the Treatment of Female Sexual Dysfunction", Drug Discovery Today, Sep. 2007, vol. 12, pp. 757-766.

Enza Lacivita et al., 5-$HT_{1A}$ Receptor, an Old Target for New Therapeutic Agents >>, Current Topics in Medical Chemistry, 2008, vol. 8, pp. 1024-1034.

Luisa de Angelis, "5-$HT_{2A}$ Antagonists in Psychiatric Disorders", Current Opinion in Investigational Drugs 2002, vol. 3(1), pp. 106-112.

Giuseppe di Giovanni et al., "Serotonin Involvement in the Basal Galglia Pathophysiology . . . ", Current Medicinal Chemistry, 2006, vol. 13, pp. 3069-3081.

Laura J. Dreshfield et al., "Enhancement of Fluoxetine-Dependent Increase of Extracellular . . . ", Neurochemical Research, 1996, vol. 21, No. 5, pp. 557-562.

Ray W. Fuller, "Uptake Inhibitors Increase Extracellular Serotonin Concentration Measured by Brain Microdyalysis", Life Sciences, 1994, vol. 55, No. 3, pp. 163-167.

Patricia W. Nance, "Alpha Adrenergic and Serotonergic Agents in the Treatment of Spastic Hyertonia", physical Medicine and Rehabilitation Clinics of North America, 2001, vol. 12, No. 4, pp. 889-905.

Ian A. Pullar et al., "In Vitro Activity of LY393558, an Inhibitor of the 5-Hydroxytryptamine Transporter . . . ", European Journal of Pharmacology, 2001, vol. 432, pp. 9-17.

D.J. Sanger, "New Perspectives for the Treatment of Disorders of Sleep and Arousal", Ann Pharm Fr, 2007, vol. 65, p. 268-274.

Kristine J. Steffen, "Emerging Drugs for Eating Disorder Treatment", Expert Opin, Emeergfing Drugs, 2006, vol. 11, No. 2, pp. 315-336.

Raffaella Zanardi et al., "How Long Should Pindolol be Associated With Paroxetine . . . ", Journal of Clinical Psychopharmacology, vol. 17, No. 6, pp. 446-450.

"Seroteonergic Mechanisms in Amyotrophic Lateral Sclerosis", intern. J. Neuroscience, 2006, vol. 116, pp. 775-826.

L. Romero et al., "Two Actions are Better Than One: Avoding Self-Inhibiton . . . ", International Clinical Psychopharmacology, 1996, vol. 11, pp. 1-8.

* cited by examiner

CHROMENONEINDOLES

SUMMARY OF THE INVENTION

The invention relates to chromenoneindole derivatives of the formula I in which
R$^1$ is H, OH, CN, Hal, CONHR, OB, CO$_2$B, CF$_3$, NR$_2$, NRCOR, NRCOOR or NRCONR$_2$,
R$^2$ is NR$_2$, NRCOR, NRCOOR, NRCONR$_2$, NO$_2$, NRSO$_2$R$_2$, NRCSR or NRCSNR$_2$,
R$^3$ is H, OH, CN, Hal, CONHR, OB, CO$_2$B, CF$_3$, NO$_2$, NR$_2$, NRCOR, NRCOOR or NRCONR$_2$,
R, independently of one another, are H, B, Het or Ar,
A is a straight-chain or branched, mono- or polyunsaturated carbon chain having 2, 3, 4, 5 or 6 C atoms,
B is a straight-chain or branched alkyl radical having 1, 2, 3, 4, 5 or 6 C atoms,
and pharmaceutically usable prodrugs, derivatives, solvates, stereo-isomers and salts thereof, including mixtures thereof in all ratios.

The invention had the object of finding novel compounds which have high bioavailability and are capable of significantly increasing the serotonin level in the brain.

It has been found that the compounds of the formula I and pharmaceutically usable prodrugs, derivatives, solvates, stereoisomers and salts thereof have valuable pharmacological properties. The compounds of the formula I exhibit particular actions on the central nervous system, in particular 5-HT reuptake-inhibiting and 5-HT$_x$-agonistic and/or -antagonistic actions, where HT$_x$ is taken to mean HT$_{1A}$, HT$_{1D}$, HT$_{2A}$ and/or HT$_{2C}$.

Compounds having a similar structure are described in DE 197 30 989. It has now been found that a group of certain chromenoneindoles, more precisely those in which R$^2$ is one of the radicals NR$_2$, NRCOR, NRCOOR, NRCONR$_2$, NO$_2$, NRSO$_2$R$_2$, NRCSR or NRCSNR$_2$, have significantly higher bioavailability compared with other chromenoneindoles and/or cause a significantly higher serotonin level in the brain (see FIGS. 1, 2 and 3). The compounds according to the invention should thus be regarded as a selection invention with respect to the said application.

Since the compounds inhibit serotonin reuptake, they are particularly suitable as antipsychotics, neuroleptics, antidepressants, anxiolytics and/or antihypertonics. The compounds exhibit serotonin-agonistic and -antagonistic properties. They inhibit the binding of tritiated serotonin ligands to hippocampal receptors (Cossery et al., European J. Pharmacol. 140 (1987), 143-155) and synaptosomal serotonin reuptake (Sherman et al., Life Sci. 23 (1978), 1863-1870). In addition, changes in DOPA accumulation in the striatum and 5-HT accumulation in various regions of the brain occur (Seyfried et al., European J. Pharmacol. 160 (1989), 31-41). The 5-HT$_{1A}$-antagonistic action is demonstrated in vitro, for example by inhibition of the abolition of electrically induced contraction of the guinea pig ileum caused by 8-OH-DPAT (Fozard and Kilbinger, Br. J. Pharmacol. 86 (1985) 601P). The 5-HT$_{1A}$-antagonistic action is detected ex vivo by inhibition of 5-HTP accumulation reduced by 8-OH-DPAT (Seyfried et al., European J. Pharmacol. 160 (1989), 31-41) and the antagonisation of 8-OH-DPAT-induced effects in the ultrasound vocalisation test (DeVry, Psychpharmacol. 121 (1995), 1-26). Inhibition of serotonin reuptake can be detected ex vivo using syntaptosomal uptake inhibition (Wong et al., Neuropsychopharmacol. 8 (1993), 23-33) and p-chloroamphetamine antagonism (Fuller et al., J. Pharmacol. Exp. Ther. 212 (1980), 115-119). Furthermore, analgesic and hypotensive actions occur.

The compounds are therefore suitable for the treatment of schizophrenia, cognitive deficits, anxiety, depression, nausea, tardive dyskinesia, gastrointestinal tract disorders, learning disorders, age-related memory disorders, psychoses and for positively influencing obsessive-compulsive disorder (OCD) and eating disorders (for example bulimia). They exhibit actions on the central nervous system, in particular additional 5-HT$_{1A}$-agonistic and 5-HT reuptake-inhibiting actions. They are likewise suitable for the prophylaxis and the combating of the consequences of cerebral infarction (apoplexia cerebri), such as strokes and cerebral ischaemia, and for the treatment of extrapyramidal motor side effects of neuroleptics and of Parkinson's disease.

The compounds of the formula I are therefore suitable both in veterinary and in human medicine for the treatment of dysfunctions of the central nervous system and of inflammation. They can be used for the prophylaxis of and for combating the consequences of cerebral infarction (apoplexia cerebri), such as strokes and cerebral ischaemia, and for the treatment of extrapyramidal motor side effects of neuroleptics and of Parkinson's disease, for the acute and symptomatic therapy of Alzheimer's disease and for the treatment of amyotrophic lateral sclerosis. They are likewise suitable as therapeutic agents for the treatment of brain and spinal cord trauma. However, they are also suitable as medicament active ingredients for anxiolytics, antidepressants, antipsychotics, neuroleptics, antihypertonics and/or for positively influencing obsessive-compulsive disorder, sleeping disorders, tardive dyskinesia, learning disorders, age-related memory disorders, eating disorders, such as bulimia, and/or sexual dysfunctions.

The invention preferably relates to compounds of the formula I in which the radical R$^1$ is CN or Hal, where CN is preferred, and R, R$^2$, R$^3$, A and B are as defined above and below for the compounds of the formula I.

Preference is furthermore given to compounds of the formula I in which the radical R$^3$ is H, where R, R$^1$, R$^2$, A and B are as defined above and below for the compounds of the formula I.

Preference is likewise given to compounds of the formula I in which the radical R$^2$ is NRCOR or NRCOOR, where R, independently of one another, can be H, B, Het or Ar, and R$^1$, R$^3$, A and B are as defined above and below for the compounds of the formula I.

Preference is also given to the compounds of the formula I in which A is (CH$_2$)$_m$, where m=2, 3, 4, 5 or 6, particularly preferably 4, and R, R$^1$, R$^2$, R$^3$ and B are as defined above and below for the compounds of the formula I.

Particular preference is given to the compounds of the formula I in which R$^1$ is CN or Hal, where CN is preferred, and R$^3$ is H, where R, R$^2$, A and B are as defined above and below for the compounds of the formula I.

Very particular preference is given to the compounds of the formula I in which $R^1$ is CN, $R^3$ is H, and A is $(CH_2)_m$, where m=4, and R, $R^2$ and B are as defined above and below for the compounds of the formula I.

In particularly preferred embodiments, the indole radical is substituted by $R^1$ in the 5-position, furthermore also in the 6- or 7-position.

In a very particularly preferred embodiment of the present invention, the compounds of the formula I are selected from the following sub-formulae Ia to Ie:

a

N-(6-{4-[4-(5-Cyano-1H-indol-3-yl)butyl]piperazin-1-yl}-2-oxo-2H-chromen-3-yl)methylamide (HCl) (EMD 391987)

b

Ethyl(6-{4-[4-(5-cyano-1H-indol-3-yl)butyl]piperazin-1-yl}-2-oxo-2H-chromen-3-yl)carbamate (EMD 480247)

c

Methyl N-(6-{4-[4-(5-cyano-1H-indol-3-yl)butyl]piperazin-1-yl}-2-oxo-2H-chromen-3-yl)carbamate (EMD 487535)

d

N-(6-{4-[4-(5-Cyano-1H-indol-3-yl)butyl]piperazin-1-yl}-2-oxo-2H-chromen-3-yl)-2,2-dimethylpropionamide (EMD 480248)

e

3-{4-[4-(3-Amino-2-oxo-2H-chromen-6-yl)piperazin-1-yl]butyl}-1H-indole-5-carbonitrile (HCl) (EMD 480246)

For all radicals which occur more than once, such as, for example, R or B, their meanings are independent of one another.

The radical B is alkyl and has 1, 2, 3, 4, 5 or 6, in particular 1, 2, 3 or 4, C atoms. Alkyl is a linear or branched alkyl radical, preferably an unbranched alkyl radical, and may be mono- or poly- by halogen (Hal), for example perfluorinated. If an alkyl radical is substituted by halogen, it preferably, depending on the number of carbon atoms in the alkyl radical, has 1, 2, 3, 4 or 5 halogen atoms. If an alkyl radical is substituted by halogen, it preferably, depending on the number of carbon atoms in the alkyl radical, has 1, 2, 3, 4 or 5 halogen atoms. Examples of alkyl groups are therefore methyl, ethyl or isopropyl, furthermore n-propyl, n-butyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore also fluoromethyl, difluoromethyl, trifluoromethyl, 1,1,1-trichloroethyl or pentafluoroethyl.

The term "aryl" covers an unsubstituted or mono- or polysubstituted aromatic mono-, bi- or tricyclic hydrocarbon radical, such as, for example, a benzene ring or anthracene, phenanthrene or naphthalene ring systems. Examples of suitable substituents include $NO_2$—, F—, Cl—, Br—, I—, HO—, $H_2N$—, $R^3HN$—, $(R^3)_2N$—, alkyl-, alkyl-O—, $CF_3$—O—, alkyl-CO—, aryl-, aryl-O—, aryl-CO—, aryl-CONH—, arylSO_2— or arylSO_2—HN—, where the substituents may occur, independently of one another, 0 to 5 times.

The term "Het" covers an unsubstituted or mono- or polysubstituted, saturated, unsaturated or aromatic mono-, bi- or tricyclic heterocyclic radical. As hetero atoms, S, N or O may occur once to three times. Examples of suitable substituents include $NO_2$—, F—, Cl—, Br—, I—, HO—, $H_2N$—, $R^3HN$—, $(R^3)_2N$—, alkyl-, alkyl-O—, $CF_3$—O—, alkyl-CO—, aryl-, aryl-O—, aryl-CO—, aryl-CONH—, aryl-$SO_2$— and aryl-$SO_2$—HN—, where the substituents may occur, independently of one another, 0 to 5 times.

The invention furthermore relates to a process for the preparation of the compounds of the formula I and pharmaceutically usable prodrugs, derivatives, solvates, stereoisomers and salts thereof, characterised in that a compound of the formula II in which R² and R³ are as defined above and below for the compounds of the formula I, is reacted with a compound of the formula III in which R¹ and A are as defined above and below for the compounds of the formula I, and L is Cl, Br, I, OH or a reactively esterified OH group or another readily nucleophilically substitutable leaving group, such as alkylsulfonyloxy having 1-6 C atoms (for example methanesulfonyloxy) or arylsulfonyloxy having 6-10 C atoms (for example benzenesulfonyloxy, p-toluenesulfonyloxy or 1- or 2-naphthalenesulfonyloxy), where I is preferred.

The present invention likewise relates to a process for the preparation of the compounds of the formula I and pharmaceutically usable prodrugs, derivatives, solvates, stereoisomers and salts thereof, characterised in that a compound of the formula IV in which R³ is as defined above and below for the compounds of the formula I, and R⁴ is an amino-protecting group or H, is reacted, in a Michael-analogous reaction, with ethyl nitroacetate and diethylammonium chloride, and the nitro group is subsequently reduced, to give the compound of the formula V and the compound of the formula V is reacted with a compound conforming to the formula III.

In addition, the compounds of the formula I are prepared by methods known per se, as described, for example, in Houben-Weyl (Methoden der Organischen Chemie [Methods of Organic Chemistry], Georg Thieme Verlag, Stuttgart; Organic Reactions, John Wiley & Sons, Inc., New York) or in DE 197 30 989, to be precise under reaction conditions as are known and suitable for the said reactions. Use can also be made here of variants which are known per se, but are not mentioned here in greater detail.

The starting materials for the claimed process may also, if desired, be formed in situ by not isolating them from the reaction mixture, but instead immediately converting them further into the compounds of the formula I.

The majority of the piperazine derivatives of the formula III are known. If they are not commercially available or known, they can be prepared by methods known per se. For example, they can be prepared by reaction of bis(2-chloroethyl)amine or bis(2-chloroethyl)ammonium chloride with amino-substituted benzopyran compounds.

The majority of the indole derivatives of the formula II are known and some are also commercially available. Furthermore, the compounds can be prepared from known compounds by electrophilic or in certain cases also nucleophilic aromatic substitutions. The starting substance used is preferably a corresponding indole-3-alkanoic acid (which can be prepared analogously to a Japp-Klingemann-type Fischer indole synthesis, cf. in this respect Böttcher et al., J. Med. Chem. 1992, 35, 4020-4026 or Iyer et al., J. Chem. Soc. Perkin Trans. II 1973, 872-878).

Primary alcohols of the formula III in which L is an OH group are obtainable, for example, by reduction of the corresponding carboxylic acids or esters thereof. Treatment with thionyl chloride, hydrogen bromide, phosphorus tribromide or similar halogen compounds gives the corresponding halides of the formula III in which L is a halogen. The corresponding sulfonyloxy compounds are obtainable from the alcohols by reaction with the corresponding sulfonyl chlorides. The iodine compounds of the formula III (L=I) are obtainable, for example, by the action of potassium iodide on the associated p-toluenesulfonic acid esters or corresponding chlorides.

Some of the starting materials of the formula IV are known. If they are not known, they can be prepared by methods known per se.

The reaction of the compounds II and III as well as V and III proceeds by methods as are known from the literature for the alkylation or acylation of amines. The components can be melted with one another without the presence of a solvent, if desired in a sealed tube or in an autoclave. However, it is also possible to react the compounds in the presence of an inert solvent. Suitable solvents are, for example, hydrocarbons, such as benzene, toluene or xylene; ketones, such as acetone or butanone; alcohols, such as methanol, ethanol, isopropanol or N-butanol; ethers, such as tetrahydrofuran (THF) or dioxane; amides, such as dimethylformamide (DMF) or N-methylpyrrolidone; nitriles, such as acetonitrile, if desired also mixtures of these solvents with one another or mixtures with water. The addition of an acid-binding agent, for example an alkali or alkaline earth metal hydroxide, carbonate or bicarbonate or another salt of a weak acid of the alkali or alkaline earth metals, preferably of potassium, sodium or calcium, or the addition of an organic base, such as triethylamine, dimethylaniline, pyridine or quinoline, or an excess of piperazine derivative of the formula II may be favourable. Depending on the conditions used, the reaction time is between a few minutes and 14 days, and the reaction temperature is between about 0 and 150°, normally between 20 and 130°.

Where appropriate, it is necessary to protect further amino groups present against alkylation or acylation by introducing suitable protecting groups before these reactions are carried out. The term "amino-protecting group" is known in general terms and relates to groups which are suitable for protecting an amino group against chemical reactions, but are easily removable after the desired chemical reaction has been carried out elsewhere in the molecule. Since protecting groups of this type and the introduction and removal thereof are well known to the person skilled in the art from numerous references and textbooks, this need not be discussed in greater detail at this point.

It is furthermore possible to obtain a compound of the formula I by treating a precursor containing one or more reducible group(s) instead of hydrogen atoms and/or one or more additional C—C and/or C—N bond(s) with a reducing agent, preferably at temperatures between −80 and +2500 in the presence of at least one inert solvent. Reducible (hydrogen-replaceable) groups are, in particular, oxygen in a carbonyl group, hydroxyl, arylsulfonyloxy (for example p-toluenesulfonyloxy), N-benzenesulfonyl, N-benzyl or O-benzyl.

It is in principle possible to convert compounds containing only one or those simultaneously containing two or more of the above-mentioned groups or additional bonds into a compound of the formula I by reduction; at the same time, substituents in the group I which are present in the starting compound can be reduced. This is preferably carried out using nascent hydrogen or complex metal hydrides, furthermore the Wolff-Kishner reduction or reduction is preferably carried out using hydrogen gas with transition-metal catalysis.

If the reducing agent used is nascent hydrogen, this can be generated, for example, by treatment of metals with weak acids or with bases. Thus, for example, a mixture of zinc with alkali metal hydroxide solution or of iron with acetic acid can be used. Also suitable is the use of sodium or another alkali metal dissolved in an alcohol, such as ethanol, isopropanol, butanol, amyl alcohol, isoamyl alcohol or phenol. It is furthermore possible to use an aluminium/nickel alloy in alkaline/aqueous solution, if desired with addition of ethanol. Sodium amalgam or aluminium amalgam in aqueous/alcoholic or aqueous solution is also suitable for generation of the nascent hydrogen. The reaction can also be carried out in the heterogeneous phase, in which case it is advantageous to use an aqueous phase and a benzene or toluene phase.

Reducing agents which can be employed are furthermore particularly advantageously complex metal hydrides, such as $LiAlH_4$, $NaBH_4$, diisobutylaluminium hydride or $NaAl(OCH_2CH_2OCH_3)_2H_2$ as well as diborane, if desired with addition of catalysts, such as $BF_3$, $AlCl_3$ or LiBr. Suitable solvents for this purpose are, in particular, ethers, such as diethyl ether, di-n-butyl ether, THF, dioxane, diglyme or 1,2-dimethoxyethane, and hydrocarbons, such as benzene. For the reduction using $NaBH_4$, suitable solvents are primarily alcohols, such as methanol or ethanol, furthermore water, and aqueous alcohols. By these methods, the reduction is preferably carried out at temperatures between −80 and +150°, in particular between about 0 and about 100°.

In addition, it is possible to carry out certain reductions through the use of $H_2$ gas with the catalytic action of transition metals, such as, for example, Raney Ni or Pd. In this way, for example, Cl, Br, I, SH or in certain cases also OH groups can be replaced by hydrogen. The $NH_2$ group in the compound of the formula V can likewise be obtained from the nitro group by catalytic hydrogenation using $Pd/H_2$ in methanol.

Compounds which otherwise conform to the formula I, but contain one or more solvolysable group(s) instead of one or more H atoms can be solvolysed, in particular hydrolysed, to the compounds of the formula I:

Furthermore, a compound of the formula I can be converted into another compound of the formula I by methods known per se.

Compounds of the formula I in which $R^1$ is a CONHR radical can be obtained by derivatisation of corresponding substituted compounds of the formula I by partial hydrolysis. It is furthermore possible firstly to hydrolyse cyano-substituted compounds of the formula I to acids and to amidate the acids using primary or secondary amines. Preference is given to the reaction of the free carboxylic acid with the amine under the conditions of a peptide synthesis. This reaction preferably succeeds in the presence of a dehydrating agent, for example a carbodiimide, such as dicyclohexylcarbodiimide or N-(3-dimethylaminopropyl)-N-ethylcarbodiimide, furthermore propanephosphonic anhydride (cf. Angew. Chem. 92, 129 (1980)), diphenylphosphoryl azide or 2-ethoxy-N-ethoxycarbonyl-1,2-dihydroquinoline, in an inert solvent, for example a halogenated hydrocarbon, such as dichloromethane, an ether, such as THF or dioxane, an amide, such as DMF or dimethylacetamide, or a nitrile, such as acetonitrile, at temperatures between about −10 and 40°, preferably between 0 and 30°. Instead of the acid or amide, it is also possible to employ reactive derivatives of these substances in the reaction, for example those in which reactive groups are temporarily blocked by protecting groups.

The acids can also be used in the form of their activated esters, which are advantageously formed in situ, for example by addition of 1-hydroxybenzotriazole or N-hydroxysuccinimide. Thus, it is also possible, for example, for cyano-substituted indole radicals to be hydrolysed to carboxyindole or carboxamidoindole radicals.

However, it is also particularly favourable to prepare the nitriles in the reverse manner, by elimination of water, starting from the amides, for example by means of trichloroacetyl chloride/$Et_3N$ [Synthesis (2), 184 (1985)] or using $POCl_3$ (J. Org. Chem. 26, 1003 (1961)).

A resultant base of the formula I can be converted into the associated acid-addition salt using an acid. Suitable acids for this reaction are those which give physiologically acceptable salts. Thus, it is possible to use inorganic acids, for example sulfuric acid, hydrohalic acids, such as hydrochloric acid or hydrobromic acid, phosphoric acids, such as orthophosphoric acid, nitric acid, sulfamic acid, furthermore organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid; benzenesulfonic acid, p-toluenesulfonic acid, naphthalene-mono- and -disulfonic acids, laurylsulfuric acid.

The free bases of the formula I can, if desired, be liberated from their salts by treatment with strong bases, such as sodium hydroxide, potassium hydroxide, sodium carbonate or potassium carbonate, so long as no further acidic groups are present in the molecule. In those cases where the compounds of the formula I contain free acid groups, salt formation can likewise be achieved by treatment with bases. Suitable bases are alkali metal hydroxides, alkaline earth metal hydroxides or organic bases in the form of primary, secondary or tertiary amines.

The pharmacological properties of the compounds of the formula I according to the invention were tested as follows:

The bioavailability was determined by a standard method described in many textbooks of pharmacokinetics with the aid of the AUC (area under the concentration/time curves) measured after po and iv administration. For the determination of the absolute bioavailability, the plasma concentration curve of the said substances was determined after intravenous (iv) and oral (po) administration to Wistar rats (male; N=3 animals/administration). The following experiment design was selected:

Administration method: iv and po
Dose: iv–0.2 mg/kg; po–0.5 mg/kg
Time of blood sampling for the determination of the plasma concentrations:
iv: 0.1, 0.5, 1, 2, 4, 6 and 24 h
po: 0.25, 0.5, 1, 2, 4, 6 and 24 h The plasma concentrations were determined with the aid of LC/MS/MS.

The plasma concentrations were used to calculate the AUC (area under the concentration/time curve) in accordance with the so-called trapezium formula.

The bioavailability is obtained from the AUC in accordance with the following formula:

Bioavailability [%]=100×(AUC po)/AUC iv)/(dose iv/dose po)

This measurement gave a bioavailability of 10% for the compound 3-(4-(4-(2-oxo-2H-1-benzopyran-6-yl)-1-piperazinyl)butyl)indole-5-carbonitrile (EMD 135894) described in DE 197 30 989.

By contrast, the bioavailability of the compound ethyl(6-{4-[4-(5-cyano-1H-indol-3-yl)butyl]piperazin-1-yl}-2-oxo-2H-chromen-3-yl)carbamate (see formula Ib; EMD 480247) was significantly higher, namely about 20%.

In order to determine the effect of the substances on the cortical serotonin level in rats in vivo, a microdialysis probe with a semipermeable membrane was implanted into the brain tissue and perfused with a solution matched to the composition of cerebrospinal fluid (see in this respect, for example, Di Chiara, Trends Pharmacol. Sci. 11, 117-121, 1990). The molecules of the extracellular space, such as, for example, also of the neurotransmitter serotonin, diffuse via this membrane into the interior of the probe in accordance with their concentration gradient. From there, they are transported with the perfusion stream to a collecting vessel. The serotonin concentration in the dialysate obtained in this way is subsequently determined by means of high-sensitivity analytical methods. The fractions obtained at regular intervals (of, for example, 15-20 minutes) thus reflect the concentration changes of the transmitter in question in the brain tissue over a period of several hours. The concentration of the serotonin in the dialysate is firstly measured without any influence. The substance to be tested is then applied, and the serotonin concentrations before and after administration of the substances are compared.

Figure 1:
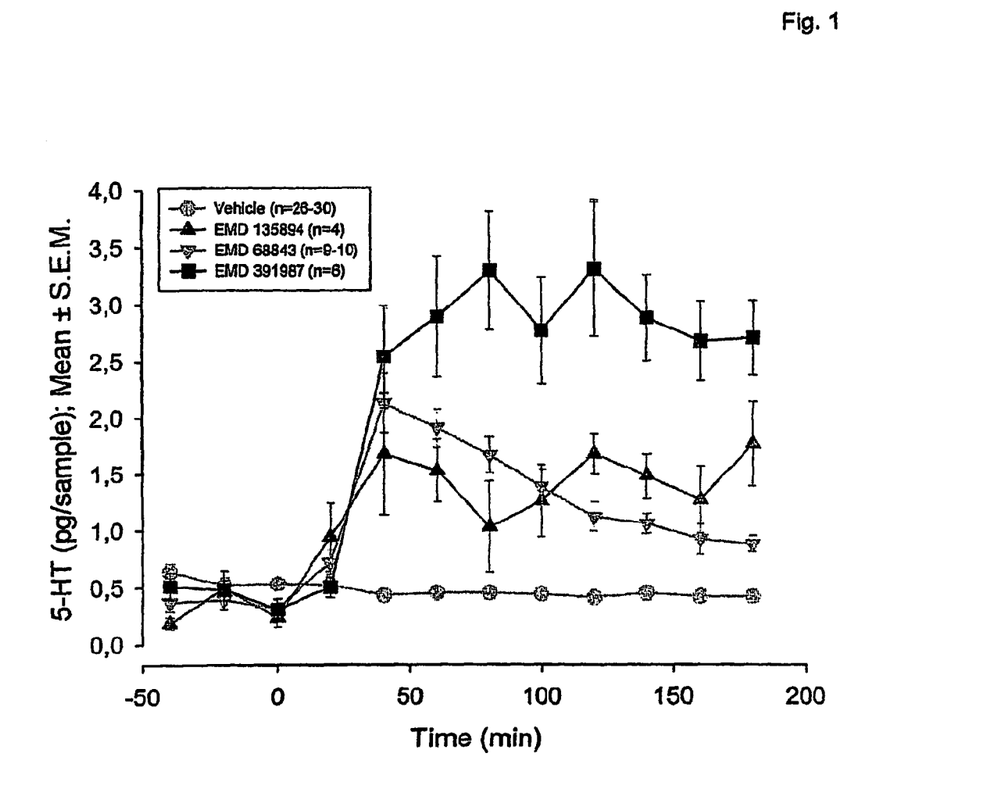
FIG. 1: Change in the serotonin concentration (5-hydroxytryptamine, 5-HT) in the dialysate as a function of time before and after administration (i.p.) of EMD 135894, EMD 68843 and EMD 391987 (concentration in each case: 1 mg/kg of body weight).

As can be seen from FIG. 1, the administration of the compound EMD 391987 (see formula Ia) results in a significantly higher serotonin level in the brain than administration of the same concentration (1 mg/kg i.p.) of the compound 3-(4-(4-(2-oxo-2H-1-benzopyran-6-yl)-1-piperazinyl)butyl)-indole-5-carbonitrile (EMD 135894), which is described in DE 197 30 989 and has been selected as comparative substance.

Vilazodone (5-{4-[4-(5-cyano-3-inolyl)butyl]-1-piperanzinyl}benzofuran-2-carboxamide; EMD 68843), which is described in EP 0 648 767 B1 and is already in clinical trials, was also employed as comparative compound since it likewise has 5-HT reuptake-inhibiting and $5\text{-HT}_x$-agonistic and/or -antagonistic properties. EMD 391987 also results in a significantly higher serotonin level in the brain compared with this compound, which causes a comparable increase in the concentration of serotonin in the brain to EMD 135894.

Figure 2:
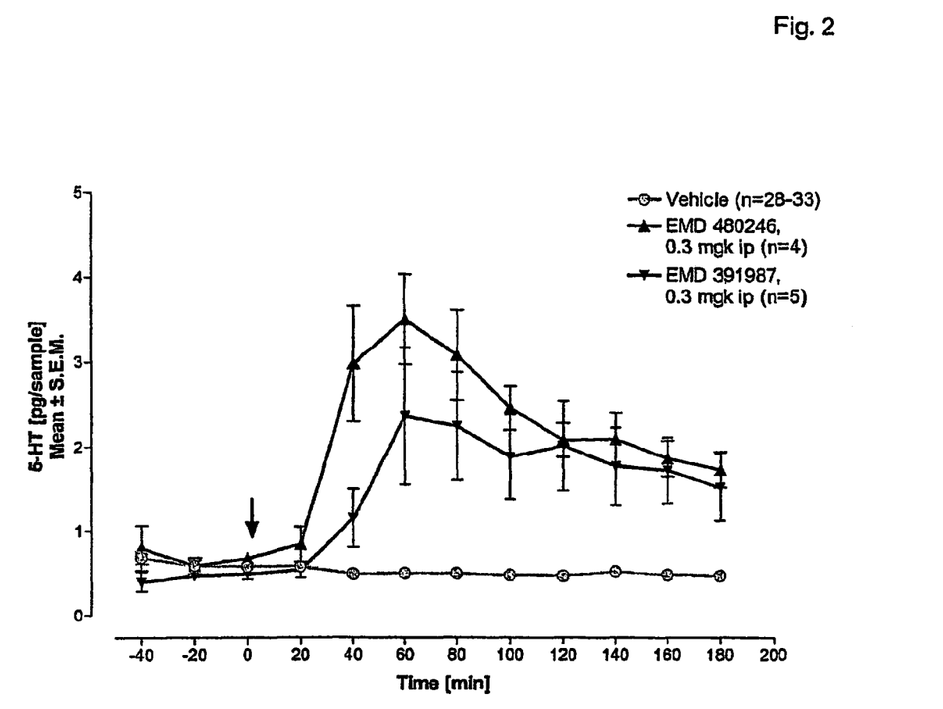
FIG. 2: Change in the serotonin concentration (5-hydroxytryptamine, 5-HT) in the dialysate as a function of time before and after administration (i.p.) of EMD 480246 and EMD 391987 (each 0.3 mg/kg of body weight).

As shown by FIG. 2, a further substance of the formula I according to the invention, 3-{4-[4-(3-amino-2-oxo-2H-chromen-6-yl)piperazin-1-yl]butyl}-1H-indole-5-carbonitrile (EMD 480246, see formula Ie), results in an even higher serotonin level than EMD 391987, which is itself superior to the comparative compounds EMD 68843 and EMD 135894.

Figure 3:
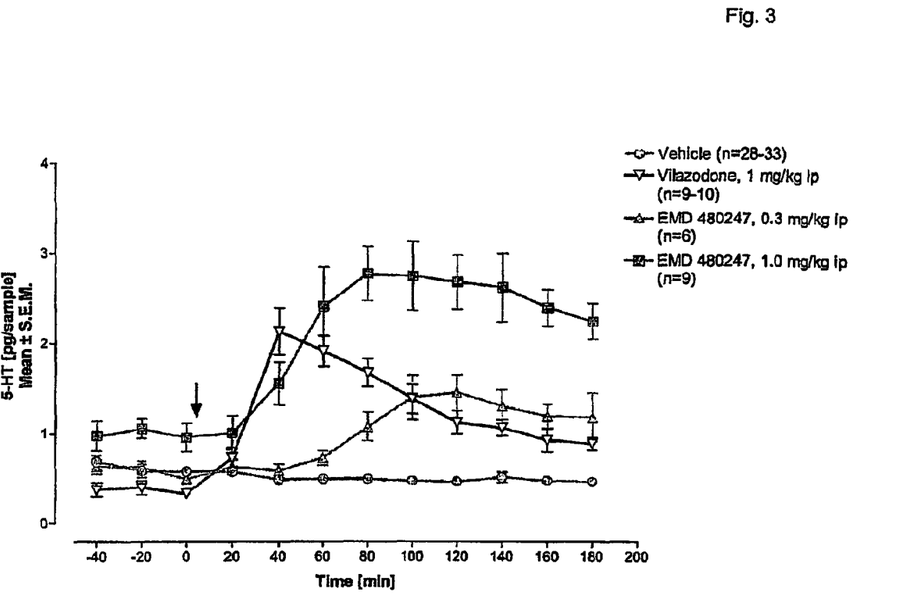
FIG. 3: Change in the serotonin concentration (5-hydroxytryptamine, 5-HT) in the dialysate as a function of time before and after administration (i.p.) of 0.3 mg/kg of body weight or 1.0 mg/kg of body weight of EMD 480247 compared with vilazodone (EMD 68843; 1 mg/kg of body weight).

Ethyl(6-{4-[4-(5-cyano-1H-indol-3-yl)butyl]piperazin-1-yl}-2-oxo-2H-chromen-3-yl)carbamate (EMD 480247, see formula Ib) also exhibits a clearly superior action to vilazodone (EMD 68843) (see FIG. 3).

Consequently, the compounds of the formula I according to the invention are clearly superior to the other compounds described in DE 197 30 989 and EP 0 648 767 B1 with respect to bioavailability and the increase in serotonin levels or inhibition of serotonin reuptake.

The invention furthermore relates to the use of the compound of the formula I and pharmaceutically usable prodrugs, derivatives, solvates, stereo-isomers and salts thereof, including mixtures thereof in all ratios, for the preparation of pharmaceutical preparations, in particular by non-chemical methods. They can be converted here, for example, into a suitable dosage form together with a solid, liquid or semi-liquid excipient or adjuvant and optionally in combination with one or more further active ingredient(s).

The invention furthermore relates to compositions, in particular pharmaceutical preparations, comprising at least one compound of the formula I and/or one of its pharmaceutically usable prodrugs, derivatives, solvates, stereoisomers and salts. These preparations can be employed as medicaments in human and veterinary medicine. Suitable carrier substances are organic or inorganic substances which are suitable for enteral (for example oral), parenteral or topical administration and do not react with the novel compounds, for example water, vegetable oils, benzyl alcohols, polyethylene glycols, gelatine, carbohydrates, such as lactose or starch, magnesium stearate, talc or Vaseline. Suitable for enteral administration are, in particular, tablets, coated tablets, capsules, syrups, juices, drops or suppositories, suitable for parenteral administration are solutions, preferably oil-based or aqueous solutions, furthermore suspensions, emulsions or implants, and suitable for topical application are ointments, creams or powders. The novel compounds may also be lyophilised and the resultant lyophilisates used, for example, for the preparation of injection preparations.

The stated preparations may be sterilised and/or comprise adjuvants, such as lubricants, preservatives, stabilisers and/or wetting agents, emulsifiers, salts for modifying the osmotic pressure, buffer substances, colorants, flavours and/or aroma substances. If desired, they may also comprise one or more further active ingredients, for example one or more vitamins.

The compounds of the formula I and pharmaceutically usable prodrugs, derivatives, solvates, stereoisomers and salts thereof can be used in the therapeutic treatment of the human or animal body and in the combating of diseases. They are suitable for the treatment of diseases of the central nervous system, such as states of tension, depression, anxiety states, schizophrenia, gastrointestinal tract disorders, nausea, tardive dyskinesia, Parkinson's disease and/or psychoses and of side effects in the treatment of hypertonia (for example using α-methyldopa). The compounds can furthermore be used in endocrinology and gynaecology, for example for the therapy of acromegalia, hypogonadism, secondary amenorrhoea, premenstrual syndrome, undesired puerperal lactation, furthermore for the prophylaxis and therapy of cerebral disorders (for example migraine), in particular in geriatrics, in a similar way to certain ergot alkaloids.

They can also particularly preferably be employed as therapeutic agents for combating the consequences of cerebral infarction (apoplexia cerebri), such as strokes and cerebral ischaemia, and for the treatment of brain and spinal cord trauma.

However, they are particularly suitable as medicament active ingredients for anxiolytics, antidepressants, antipsychotics, neuroleptics, antihypertonics and/or for positively influencing obsessive-compulsive disorder (OCD), sleeping disorders, tardive dyskinesia, learning disorders, age-related memory disorders, eating disorders, such as bulimia, and/or sexual dysfunctions.

The substances according to the invention are generally administered analogously to known commercially available preparations (for example citalopram and fluoxetine), preferably in doses of between about 0.2 and 500 mg, in particular between 0.2 and 50 mg, per dosage unit. The daily dose is preferably between about 0.001 and 10 mg/kg of body weight. The low doses are between about 0.2 and 500 mg, in particular between 0.2 and 50 mg, per dosage unit. The low doses (about 0.2 to 1 mg per dosage unit; about 0.001 to 0.005 mg/kg of body weight) are particularly suitable for use as migraine agents; for the other indications, doses of between 10 and 50 mg per dosage unit are preferred. However, the specific dose for each particular patient depends on a very wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

EXAMPLES

Example 1

Synthesis of N-(6-{4-[4-(5-cyano-1H-indol-3-yl)butyl]piperazin-1-yl}-2-oxo-2H-chromen-3-yl)methylamide a)

20.0 g (91.7 mmol) of 1 were initially introduced in chlorobenzene (600 ml), 16.4 g (91.7 mmol) of bis(2-chloroethyl)ammonium chloride and 12.7 g mg (92.0 mmol) of potassium carbonate were added, and the mixture was refluxed for 4 days. The residue was filtered off, washed with copious water and dried in a vacuum drying cabinet.

Yield: 14 g of colourless solid (2)

[M+H]$^+$ 288 (HPLC-MS)

b)

3 (150 g, 0.65 mol) was dissolved in 500 ml of acetone (dried), and sodium iodide (580 g, 3.87 mol) was stirred in. The suspension was stirred at RT. After 118 hours, a further 18 g of NaI (0.12 mol) were added, and the mixture was stirred at RT for a further 3 days. The suspension was filtered off with suction, rinsed with acetone (dried), and 100 g of NaI (ground in a mortar) were added, and the mixture was stirred at RT. After 24 hours, a further 100 g of NaI (ground in a mortar) were added, and the mixture was stirred for a further 72 hours. A further 100 g of NaI (ground in a mortar) were subsequently added, and the mixture was stirred for a further 5 days. The suspension was filtered off with suction and rinsed well with acetone, the filter cake was discarded, and the filtrate was evaporated to dryness. The residue was stirred with water and extracted by shaking with ethyl acetate, and the ethyl acetate solution was dried, filtered and evaporated to dryness. The residue was stirred with a mixture of 300 ml of petroleum ether and 200 ml of diethyl ether and filtered off with suction. The crystals were rinsed on the suction filter with 50 ml of cold diethyl ether and dried in air.

Yield: 184 g of brownish crystals (4)

[M+H]$^+$ 325 (HPLC-MS)

c)

12.4 g (43.0 mmol) of 2 were taken up in N-methylpyrrolidone (150 ml), 13.9 g (43.0 mmol) of 4 and 11.1 g (85.8 mmol) of diisopropyldiethylamine were added, and the mixture was stirred at 140° C. for 3 days. The reaction solution was poured into ice-water, and the brown precipitate was filtered off. The residue was purified by column chromatography (ethyl acetate/MeOH, 9:1), and the virtually clean fraction was recrystallised from tert-butyl methyl ether/hexane. The solid was converted into the hydrochloride in the usual manner.

Yield: 3.8 g of colourless solid, HCl salt (5)

[M+H]$^+$ 484 (HPLC-MS)

Example 2

Synthesis of N -(6-{4-[4-(5-cyano-1H-indol-3-yl)butyl]piperazin-1-yl}-2-oxo-2H-chromen -3-yl)carbamate 6 (20.0 g, 65.1 mmol), ethyl nitroacetate (9.00 ml, 78.3 mmol) and diethyl-ammonium chloride (8.58 g, 78.3 mmol) were heated on a water separator for 3 days in toluene (500 ml). The cooled reaction solution was washed with water and dried, the drying agent was filtered off, and the solvent was removed. The residue was purified by column chromatography (ethyl acetate/cyclohexane)

Yield: 13.2 g of yellowish solid (7)

[M+H]$^+$ 376, [M-55]$^+$ 320 (HPLC-MS)

7 (3.00 g, 7.99 mmol) was dissolved in MeOH (50 ml), Pd/C.5% (1 g) was added, and the mixture was stirred for 24 hours in a hydrogen atmosphere. The catalyst was filtered off, and the filtrate was evaporated to dryness. The residue was purified by column chromatography (ethyl acetate/methanol).

Yield: 1.50 g of brownish solid (8)

[M+H]$^+$ 346, [M-55]$^+$ 290 (HPLC-MS)

8 (375 mg, 1.09 mmol) was dissolved in dichloromethane (10 ml), pyridine (0.11 ml, 1.1 mmol) was added, and the mixture was cooled to 0° C. Ethyl chloroformate (141 mg, 1.10 mmol) was added dropwise at this temperature, and the mixture was stirred overnight at room temperature. The batch was evaporated and purified by column chromatography (ethyl acetate/cyclohexane, 1:1).

Yield: 320 mg of colourless solid

[M+H]$^+$ 418, [M-55]$^+$ 362 (HPLC-MS)

The substance obtained in this way was stirred for 60 minutes at room temperature in saturated ethanolic HCl solution (10 ml), and the solvent was stripped off.

Yield: 270 mg of colourless solid, di-HCl salt (9)

[M+H]$^+$ 355 (HPLC-MS)

9 (200 mg, 0.51 mmol), 4 (see Example 1; 166 mg, 0.51 mmol) and diisopropylethylamine (0.26 ml, 1.53 mmol) were refluxed for 18 hours in acetonitrile (5 ml). The solvent was removed, and the residue and purified by column chromatography (ethyl acetate/methanol). The solid was converted into the hydrochloride in the usual manner.

Yield: 70 mg of colourless solid, HCl salt (10)
[M+H]$^+$ 514 (HPLC-MS)

Example 3

Synthesis of N-(6-{4-[4-(5-cyano-1H-indol-3-yl)butyl]piperazin-1-yl}-2-oxo-2H-chromen-3-yl)amine Compound 8 was prepared analogously to steps a) and b) in Example 2. 8 (1.00 g, 2.90 mmol) was subsequently stirred at room temperature for 60 minutes in saturated ethanolic HCl solution (10 ml), and the solvent was stripped off.

Yield: 880 mg of colourless solid, di-HCl salt (8)
[M+H]$^+$ 246 (HPLC-MS) Compound 8 obtained in this way (50 mg, 0.16 mmol) was refluxed for 18 hours with 4 (77 mg, 0.24 mmol) and diisopropylethylamine (0.08 ml, 0.47 mmol) in acetonitrile (2 ml). The solvent was removed, and the residue and purified by column chromatography (ethyl acetate/methanol). The solid was converted into the hydrochloride in the usual manner.

Yield: 25 mg of colourless solid, HCl salt (11)
[M+H]$^+$ 442 (HPLC-MS)

Example A

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

Example B

Solution

A solution is prepared from 1 g of an active ingredient of the formula I, 9.38 g of NaH$_2$PO$_4$×2H$_2$O, 28.48 g of NaH$_2$PO$_4$×12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example C

Ointment 500 mg of an active ingredient of the formula I are mixed with 99.5 g of Vaseline under aseptic conditions.

Example D

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet comprises 10 mg of active ingredient.

Example E

Coated Tablets

Tablets are pressed analogously to Example D and are subsequently coated in a conventional manner with a coating of sucrose, potato starch, talc, tragacanth and dye.

Example F

Capsules 2 kg of active ingredient of the formula I are introduced into hard gelatine capsules in a conventional manner in such a way that each capsule contains 20 mg of the active ingredient.

Example G

Ampoules

A solution of 1 kg of active ingredient of the formula I in 60 l of bidistilled water is transferred into ampoules, lyophilised under aseptic conditions and sealed under sterile conditions. Each ampoule contains 10 mg of active ingredient.

The invention claimed is:

1. Compounds of the formula I in which
R$^1$ is H, OH, CN, Hal, CONHR, OB, CO$_2$B, CF$_3$, NR$_2$, NRCOR, NRCOOR or NRCONR$_2$,
R$^2$ is NR$_2$, NRCOR, NRCOOR, NRCONR$_2$, NO$_2$, NRSO$_2$R$_2$, NRCSR or NRCSNR$_2$,
R$^3$ is H, OH, CN, Hal, CONHR, OB, CO$_2$B, CF$_3$, NO$_2$, NR$_2$, NRCOR, NRCOOR or NRCONR$_2$,
R, independently of one another, are H, B, Het or Ar,
A is a straight-chain or branched, mono- or polyunsaturated carbon chain having 2, 3, 4, 5, or 6 carbon atoms,
B is a straight-chain or branched alkyl radical having 1, 2, 3, 4, 5 or 6 carbon atoms,
a pharmaceutically acceptable salt thereof.

2. A compounds of the formula I according to claim 1, wherein R$^1$ is CN or Hal.

3. A compounds of the formula I according to claim 1, wherein R$^3$ is H.

4. A compounds of the formula I according to claim 1 wherein R$^2$ is NRCOR or NRCOOR.

5. A compounds of the formula I according to claim 1, wherein A is (CH$_2$)$_m$, where m=2, 3, 4, 5 or 6.

6. A compounds of the formula I according to claim 1, wherein R$^1$ is CN or Hal, and R$^3$ is H.

7. A compounds of the formula I according to claim 1, wherein R$^1$ is CN, R$^3$ is H, and A is (CH$_2$)$_m$, where m=4.

8. A compounds of the formula I according to claim 1, wherein R$^1$ is in position 5 of the indole radical.

9. A compound which is
N-(6-{4-[4-(5-cyano-1H-indol-3-yl)butyl]piperazin-1-yl}-2-oxo-2H-chromen-3-yl)methylamide,
ethyl(6-{4-[4-(5-cyano-1H-indol-3-yl)butyl]piperazin-1-yl}-2-oxo-2H-chromen-3-yl)carbamate,
methyl N-(6-{4-[4-(5-cyano-1H-indol-3-yl)butyl]piperazin-1-yl}-2-oxo-2H-chromen-3-yl)carbamate,
N-(6-{4-[4-(5-cyano-1H-indol-3-yl)butyl]piperazin-1-yl}-2-oxo-2H-chromen-3-yl)-2,2-dimethylpropionamide,
3-{4-[4-(3-amino-2-oxo-2H-chromen-6-yl)piperazin-1-yl]butyl}-1H-indole-5-carbonitrile,
or a pharmaceutically acceptable salt thereof.

10. A process for the preparation of compound of the formula I according to claim 1, comprising reacting a compound of formula II in which R$^2$ and R$^3$ are as defined in claim 1, with a compound of formula III in which R$^1$ and A are as defined in claim 1, and L is Cl, Br, I, OH or a reactively esterified OH group or another readily nucleophilically substitutable leaving group.

11. A process for the preparation of compounds of the formula I according to claim 1, comprising reacting a compound of formula IV in which R$^3$ is as defined in claim 1, and R$^4$ is an amino-protecting group or H, in a Michael-analogous reaction, with ethyl nitroacetate and diethylammonium chloride, and subsequently reducing the nitro group to give a compound of the formula V and reacting the compound of formula V with a compound conforming to formula III in which R$^1$ and A are as defined in claim 1, and L is Cl, Br, I, OH or a reactively esterified OH group or another readily nucleophilically substitutable leaving group.

12. A pharmaceutical composition, comprising an effective amount of a compound of the formula I, and a pharmaceutically acceptable carrier according to claim 1, optionally in addition to one or more inert excipients, adjuvants and/or diluents.

13. A process for the preparation of a composition according to claim 12, comprising combining a compound of the formula I with one or more inert excipients and/or diluents by non-chemical methods.

14. A method for treating depression comprising administering to a host in need thereof a compound according to claim 1.

15. A method for treating schizophrenia, comprising administering to a host in need thereof a compound according to claim 1.

* * * * *

UNITED STATES PATENT AND TRADEMARK OFFICE
CERTIFICATE OF CORRECTION

| | | |
|---|---|---|
| PATENT NO. | : 7,968,551 B2 | |
| APPLICATION NO. | : 10/551997 | |
| DATED | : June 28, 2011 | |
| INVENTOR(S) | : Schiemann et al. | |

It is certified that error appears in the above-identified patent and that said Letters Patent is hereby corrected as shown below:

Column 17, line 27 reads "2. A compounds of the formula I according to claim 1," should read -- 2. A compound of the formula I according to claim 1, --

Column 17, line 29 reads "3. A compounds of the formula I according to claim 1," should read -- 3. A compound of the formula I according to claim 1, --

Column 17, line 31 reads "4. A compounds of the formula I according to claim 1" should read -- 4. A compound of the formula I according to claim 1 --

Column 17, line 33 reads "5. A compounds of the formula I according to claim 1," should read -- 5. A compound of the formula I according to claim 1, --

Column 17, line 35 reads "6. A compounds of the formula I according to claim 1," should read -- 6. A compound of the formula I according to claim 1, --

Column 17, line 37 reads "7. A compounds of the formula I according to claim 1," should read -- 7. A compound of the formula I according to claim 1, --

Column 17, line 39 reads "8. A compounds of the formula I according to claim 1, should read -- 8. A compound of the formula I according to claim 1, --

Signed and Sealed this
Eighth Day of November, 2011

David J. Kappos
*Director of the United States Patent and Trademark Office*